United States Patent
Brown et al.

(10) Patent No.: US 10,640,403 B2
(45) Date of Patent: May 5, 2020

(54) ANTIMICROBIAL BATCH DILUTION SYSTEM

(71) Applicant: Applied Silver, Inc., Hayward, CA (US)

(72) Inventors: David E. Brown, Danville, CA (US); Sean Morham, Napa, CA (US)

(73) Assignee: Applied Silver, Inc., Hayward, CA (US)

( * ) Notice: Subject to any disclaimer, the term of this patent is extended or adjusted under 35 U.S.C. 154(b) by 355 days.

(21) Appl. No.: 15/180,908

(22) Filed: Jun. 13, 2016

(65) Prior Publication Data

US 2017/0008783 A1  Jan. 12, 2017

Related U.S. Application Data

(63) Continuation-in-part of application No. 14/099,066, filed on Dec. 6, 2013, now Pat. No. 9,364,798, which
(Continued)

(51) Int. Cl.
*A61L 2/18* (2006.01)
*C02F 1/50* (2006.01)
(Continued)

(52) U.S. Cl.
CPC ............... *C02F 1/505* (2013.01); *A61L 2/18* (2013.01); *B01F 1/0027* (2013.01); *C02F 1/008* (2013.01);
(Continued)

(58) Field of Classification Search
CPC combination set(s) only.
See application file for complete search history.

(56) References Cited

U.S. PATENT DOCUMENTS 3,751,885 A    8/1973  McNeely
3,841,116 A *  10/1974 Klein ................... D06F 31/00
                                                     210/167.3
(Continued)

FOREIGN PATENT DOCUMENTS

CH      698955      12/2009
CN      1218009     6/1999
(Continued)

OTHER PUBLICATIONS

FilterWaterDirect. "Hard Water can easily be treated before it damages fixtures and appliances in your home". Wayback Machine capture from Jan. 26, 2010 (Year: 2010).*
(Continued)

*Primary Examiner* — Donald R Spamer
(74) *Attorney, Agent, or Firm* — McDonnell Boehnen Hulbert & Berghoff LLP

(57) ABSTRACT

An antimicrobial supply system employs a process water supply and incorporates a metallic ion supply connected to the process water supply to provide a high ion concentrate to an output. A dilution reservoir is connected to the metallic ion supply output and has an input from the process water supply. A pump is connected to an output of the reservoir. A manifold connected to the pump provides a dilute concentrate to at least one washing system and a recirculation loop to the dilution reservoir for enhanced mixing of the dilute concentrate. An electronics control module is connected to a first flow controller between the process water supply and the metallic ion supply and a second flow controller between the metallic ion supply and the reservoir for dilution control establishing a desired metallic ion concentration.

14 Claims, 6 Drawing Sheets

Related U.S. Application Data is a continuation-in-part of application No. 13/968,084, filed on Aug. 15, 2013.

(51) Int. Cl.

| | | |
|---|---|---|
| *C02F 1/00* | (2006.01) | |
| *C02F 9/00* | (2006.01) | |
| *B01F 1/00* | (2006.01) | |
| *G05D 11/13* | (2006.01) | |
| C02F 1/44 | (2006.01) | |
| C02F 1/28 | (2006.01) | |
| D06F 39/00 | (2020.01) | |
| C02F 1/74 | (2006.01) | |
| D06F 31/00 | (2006.01) | |
| D06F 35/00 | (2006.01) | |
| D06F 39/02 | (2006.01) | |

(52) U.S. Cl.
CPC .............. *C02F 9/00* (2013.01); *G05D 11/132* (2013.01); *A61L 2202/14* (2013.01); *A61L 2202/15* (2013.01); *A61L 2202/17* (2013.01); *A61L 2202/26* (2013.01); *C02F 1/283* (2013.01); *C02F 1/441* (2013.01); *C02F 1/74* (2013.01); *C02F 2209/006* (2013.01); *C02F 2209/02* (2013.01); *C02F 2209/03* (2013.01); *C02F 2209/40* (2013.01); *C02F 2303/04* (2013.01); *D06F 31/00* (2013.01); *D06F 35/008* (2013.01); *D06F 39/00* (2013.01); *D06F 39/022* (2013.01); *Y10T 137/4891* (2015.04)

(56) References Cited

U.S. PATENT DOCUMENTS

| | | |
|---|---|---|
| 4,048,032 A | 9/1977 | Eibl |
| 4,098,660 A | 7/1978 | Eibl et al. |
| 4,119,518 A | 10/1978 | Miller |
| 4,145,291 A | 3/1979 | Console et al. |
| 4,198,296 A | 4/1980 | Doumas et al. |
| 4,525,253 A | 6/1985 | Hayes et al. |
| 4,545,956 A | 10/1985 | Ciszewski et al. |
| 4,696,742 A | 9/1987 | Shimazaki |
| 4,710,282 A | 12/1987 | Chak et al. |
| 4,755,268 A | 7/1988 | Matsuo et al. |
| 4,889,644 A * | 12/1989 | Amberg .................. C11D 1/83 8/137 |
| 4,933,870 A | 6/1990 | Chang |
| 4,995,975 A | 2/1991 | Jacquot et al. |
| 5,190,659 A | 3/1993 | Wang et al. |
| 5,281,312 A | 1/1994 | Woodside |
| 5,342,528 A | 8/1994 | Adachi et al. |
| 5,364,512 A | 11/1994 | Earl |
| 5,632,904 A | 5/1997 | Samad et al. |
| 5,765,403 A | 6/1998 | Lincoln et al. |
| 5,782,109 A | 7/1998 | Spriggs et al. |
| 5,787,537 A | 8/1998 | Mannillo |
| 5,829,275 A * | 11/1998 | Babuin ................. D06F 39/082 68/12.13 |
| 5,843,284 A | 12/1998 | Waters et al. |
| 5,858,246 A | 1/1999 | Rafter et al. |
| 6,022,459 A | 2/2000 | Briggs et al. |
| 6,128,931 A | 10/2000 | Woods |
| 6,254,894 B1 | 7/2001 | Denkewicz, Jr. et al. |
| 6,267,885 B1 | 7/2001 | Briggs et al. |
| 6,303,039 B1 | 10/2001 | Back et al. |
| 6,398,927 B1 | 6/2002 | Merzhauser |
| 6,508,929 B1 | 1/2003 | Mercer |
| 6,514,406 B1 | 2/2003 | Katehis |
| 6,524,540 B1 | 2/2003 | Heinig, Jr. |
| 6,562,243 B2 | 5/2003 | Sherman |
| 6,634,048 B1 | 10/2003 | Hornung et al. |
| 6,641,829 B1 | 11/2003 | Green et al. |
| 6,761,827 B2 | 7/2004 | Coffey |
| 6,838,095 B2 | 1/2005 | Newman et al. |
| 6,929,740 B2 | 8/2005 | Hayes |
| 6,982,039 B1 | 1/2006 | Butkus et al. |
| 7,012,053 B1 | 3/2006 | Barnabus et al. |
| 7,152,759 B2 | 12/2006 | Walton |
| 7,322,065 B2 | 1/2008 | Kim et al. |
| 7,384,564 B2 | 6/2008 | Bo |
| 7,413,667 B1 | 8/2008 | Routberg et al. |
| 7,422,759 B2 | 9/2008 | Kepner et al. |
| 7,481,081 B2 | 1/2009 | Hsu et al. |
| 7,487,876 B2 | 2/2009 | Maeda |
| 7,540,966 B2 | 6/2009 | Costa et al. |
| 7,597,718 B2 | 10/2009 | Yoshikawa et al. |
| 7,617,704 B2 | 11/2009 | Iimori et al. |
| 7,624,601 B2 | 12/2009 | Ikemizu et al. |
| 7,708,896 B2 | 5/2010 | Ooe et al. |
| 7,807,199 B2 | 10/2010 | Allen et al. |
| 7,807,661 B2 | 10/2010 | Ylitalo et al. |
| 7,819,127 B1 | 10/2010 | Huffman |
| 7,882,647 B2 | 2/2011 | Ikemizu |
| 7,934,402 B2 | 5/2011 | Lee |
| 7,942,024 B2 | 5/2011 | Lee |
| 7,950,254 B2 | 5/2011 | Gray et al. |
| 7,972,519 B2 | 7/2011 | Koos et al. |
| 8,002,898 B2 | 8/2011 | Schepers et al. |
| 8,118,912 B2 | 2/2012 | Rodriguez et al. |
| 8,173,067 B2 | 5/2012 | Eldred |
| 8,239,990 B2 | 8/2012 | Lim et al. |
| 8,309,506 B2 | 11/2012 | Sunder et al. |
| 8,361,505 B1 | 1/2013 | Perry |
| 8,394,420 B2 | 3/2013 | Kepner et al. |
| 8,449,732 B2 | 5/2013 | Choi |
| 8,460,395 B2 | 6/2013 | Smulowitz |
| 8,563,447 B2 | 10/2013 | Canada |
| 8,641,947 B2 | 2/2014 | Schmuhl et al. |
| 8,729,008 B2 | 5/2014 | Begli et al. |
| 9,132,296 B2 | 9/2015 | Wingfield |
| 2001/0049846 A1 | 12/2001 | Guzzi et al. |
| 2002/0189954 A1 | 12/2002 | Miyazaki et al. |
| 2003/0170453 A1 | 9/2003 | Foss et al. |
| 2003/0176928 A1 * | 9/2003 | Lee .................. D06F 33/02 700/11 |
| 2003/0190370 A1 | 10/2003 | Kim et al. |
| 2003/0196282 A1 | 10/2003 | Fyvie et al. |
| 2003/0229474 A1 * | 12/2003 | Suzuki ............ G08B 13/19623 702/188 |
| 2003/0230122 A1 | 12/2003 | Lee |
| 2004/0025263 A1 | 2/2004 | Kim et al. |
| 2004/0031764 A1 | 2/2004 | Heinig, Jr. |
| 2004/0205899 A1 | 10/2004 | Park et al. |
| 2004/0214495 A1 | 10/2004 | Foss et al. |
| 2005/0019568 A1 | 1/2005 | Foss et al. |
| 2005/0037057 A1 | 2/2005 | Schuette et al. |
| 2005/0095158 A1 | 5/2005 | Kirschner et al. |
| 2005/0118281 A1 | 6/2005 | Newman et al. |
| 2005/0155939 A1 | 7/2005 | Stadelmann |
| 2005/0188731 A1 | 9/2005 | Aouad |
| 2005/0194297 A1 | 9/2005 | Dorward |
| 2005/0224419 A1 | 10/2005 | Wien et al. |
| 2005/0252255 A1 * | 11/2005 | Gray .................. B01D 61/147 68/145 |
| 2006/0110258 A1 | 5/2006 | Iimura et al. |
| 2006/0123562 A1 | 6/2006 | Ghosh et al. |
| 2006/0127457 A1 | 6/2006 | Buchalter |
| 2006/0130533 A1 | 6/2006 | Ooe et al. |
| 2006/0163135 A1 * | 7/2006 | Ellis .................. D06F 35/001 210/251 |
| 2006/0164093 A1 | 7/2006 | Ooe |
| 2006/0265814 A1 | 11/2006 | Ritter |
| 2007/0004300 A1 | 1/2007 | Kreider et al. |
| 2007/0044820 A1 | 3/2007 | Chan et al. |
| 2007/0045176 A1 | 3/2007 | Chandra et al. |
| 2007/0134301 A1 | 6/2007 | Ylitalo et al. |
| 2007/0163097 A1 | 7/2007 | Metcalfe et al. |
| 2007/0175833 A1 | 8/2007 | Ikeboh et al. |
| 2007/0243380 A1 | 10/2007 | Vegad et al. |
| 2007/0243781 A1 | 10/2007 | Chou |
| 2008/0016919 A1 | 1/2008 | Lee |

(56) References Cited

U.S. PATENT DOCUMENTS

| | | | |
|---|---|---|---|
| 2008/0023385 A1 | 1/2008 | Baker, Jr. et al. |
| 2008/0041117 A1 | 2/2008 | Lee |
| 2008/0085326 A1 | 4/2008 | Ruan |
| 2008/0131471 A1 | 6/2008 | Kolbe et al. |
| 2008/0217807 A1 | 9/2008 | Lee et al. |
| 2008/0248075 A1 | 10/2008 | Brambilla et al. |
| 2008/0256719 A1 | 10/2008 | Radev |
| 2008/0267812 A1* | 10/2008 | Kawachi ............... A61L 2/18 422/3 |
| 2008/0299006 A1 | 12/2008 | Ikemizu |
| 2008/0302713 A1 | 12/2008 | Patrick |
| 2009/0000040 A1 | 1/2009 | Ikemizu |
| 2009/0104239 A1 | 4/2009 | Parsons et al. |
| 2009/0181592 A1 | 7/2009 | Dugan |
| 2009/0193593 A1 | 8/2009 | Kirigakubo et al. |
| 2009/0194562 A1* | 8/2009 | Kessler ............... A47L 15/0055 222/1 |
| 2009/0218266 A1 | 9/2009 | Sawafta et al. |
| 2009/0259157 A1 | 10/2009 | Thomas |
| 2010/0000268 A1 | 1/2010 | Kohne |
| 2010/0047321 A1 | 2/2010 | Sandford et al. |
| 2010/0050872 A1 | 3/2010 | Lee |
| 2010/0102002 A1 | 4/2010 | O'Brien et al. |
| 2010/0116689 A1 | 5/2010 | Greene et al. |
| 2010/0140185 A1 | 6/2010 | Hill |
| 2010/0183739 A1 | 7/2010 | Newman |
| 2010/0193449 A1 | 8/2010 | Shang et al. |
| 2010/0243432 A1 | 9/2010 | Ikemizu |
| 2011/0017609 A1 | 1/2011 | Choi |
| 2011/0094972 A1 | 4/2011 | King et al. |
| 2011/0100838 A1 | 5/2011 | Kim et al. |
| 2011/0120921 A1 | 5/2011 | Kim |
| 2011/0139632 A1 | 6/2011 | Beringer et al. |
| 2011/0120423 A1 | 7/2011 | Barry et al. |
| 2011/0224120 A1 | 9/2011 | Meine et al. |
| 2011/0262556 A1 | 10/2011 | Holladay et al. |
| 2011/0297609 A1 | 12/2011 | Hu |
| 2012/0003326 A1 | 1/2012 | Meine et al. |
| 2012/0055862 A1 | 3/2012 | Parekh et al. |
| 2012/0091070 A1 | 4/2012 | Sjaunta et al. |
| 2012/0187052 A1 | 7/2012 | Elliott |
| 2012/0192363 A1 | 8/2012 | King |
| 2012/0213665 A1 | 8/2012 | Bik et al. |
| 2013/0022686 A1 | 1/2013 | Rademan et al. |
| 2013/0281345 A1 | 10/2013 | Burkinshaw et al. |
| 2013/0327419 A1 | 12/2013 | Morham |
| 2014/0202943 A1 | 7/2014 | Pradeep et al. |
| 2014/0369953 A1 | 12/2014 | Purschwitz et al. |
| 2015/0047718 A1 | 2/2015 | Brown et al. |
| 2015/0159314 A1 | 6/2015 | Morham et al. |
| 2015/0159319 A1 | 6/2015 | Morris et al. |

FOREIGN PATENT DOCUMENTS

| | | |
|---|---|---|
| CN | 1558016 | 12/2004 |
| CN | 1671911 | 9/2005 |
| CN | 2725278 | 9/2005 |
| CN | 2753774 | 1/2006 |
| CN | 2780804 | 5/2006 |
| CN | 200984347 | 12/2007 |
| CN | 101411958 | 4/2008 |
| CN | 201056507 | 5/2008 |
| CN | 101307555 | 11/2008 |
| CN | 201254480 | 6/2009 |
| CN | 101670123 | 3/2010 |
| CN | 101731269 | 6/2010 |
| CN | 101863581 | 10/2010 |
| CN | 101864670 | 10/2010 |
| CN | 101926363 | 12/2010 |
| CN | 101967025 | 2/2011 |
| CN | 201737797 | 2/2011 |
| CN | 201738163 | 2/2011 |
| CN | 101991870 | 3/2011 |
| CN | 201791121 | 4/2011 |
| CN | 201873556 | 6/2011 |
| CN | 201902711 | 7/2011 |
| CN | 202021117 | 11/2011 |
| CN | 202023990 | 11/2011 |
| CN | 202036069 | 11/2011 |
| CN | 102330844 | 1/2012 |
| CN | 202121806 | 1/2012 |
| CN | 102421295 | 4/2012 |
| CN | 102535114 | 7/2012 |
| CN | 202386643 | 8/2012 |
| CN | 202390678 | 8/2012 |
| CN | 102666397 | 9/2012 |
| CN | 202410344 | 9/2012 |
| CN | 202430491 | 9/2012 |
| CN | 102781814 | 11/2012 |
| DE | 19853193 | 5/2000 |
| DE | 102007034215 | 5/2008 |
| EP | 0128782 | 11/1987 |
| EP | 1296895 | 4/2003 |
| EP | 1334073 | 8/2003 |
| EP | 1600545 | 11/2005 |
| EP | 1785518 | 5/2007 |
| EP | 1983085 A1 | 10/2008 |
| EP | 2045389 | 4/2009 |
| EP | 2461676 | 6/2012 |
| EP | 2499916 | 9/2012 |
| EP | 2513370 | 10/2012 |
| EP | 2544804 | 1/2013 |
| EP | 2674523 | 12/2013 |
| GB | 2298858 | 3/1995 |
| GB | 2419590 | 5/2006 |
| JP | H0560721 | 3/1993 |
| JP | 2001025772 | 1/2001 |
| JP | 2001062458 | 3/2001 |
| JP | 2001066090 | 3/2001 |
| JP | 2001276484 | 10/2001 |
| JP | 2001340281 | 12/2001 |
| JP | 2002113288 | 4/2002 |
| JP | 2004057423 | 2/2004 |
| JP | 2004105692 | 4/2004 |
| JP | 2004313752 | 11/2004 |
| JP | 2004346024 | 12/2004 |
| JP | 2005098606 | 4/2005 |
| JP | 2005261830 | 9/2005 |
| JP | 2005296671 | 10/2005 |
| JP | 2007061757 | 3/2007 |
| JP | 2007167785 | 7/2007 |
| JP | 2008119287 | 5/2008 |
| JP | 2008183283 | 8/2008 |
| JP | 2008220450 | 9/2008 |
| JP | 2008279056 | 11/2008 |
| JP | 2009017907 | 1/2009 |
| JP | 2009039320 | 2/2009 |
| JP | 2010136738 | 6/2010 |
| JP | 2010136739 | 6/2010 |
| JP | 2010194484 | 9/2010 |
| JP | 2012161728 | 8/2012 |
| JP | 2014176448 | 9/2014 |
| KR | 1990069099 | 9/1999 |
| KR | 20000037120 | 7/2000 |
| KR | 20020012369 | 2/2002 |
| KR | 20020074306 | 9/2002 |
| KR | 20040085107 | 10/2004 |
| KR | 20040093957 | 11/2004 |
| KR | 20050004614 | 1/2005 |
| KR | 20050004616 | 1/2005 |
| KR | 20050004618 | 1/2005 |
| KR | 20050004620 | 1/2005 |
| KR | 20050004621 | 1/2005 |
| KR | 20050004623 | 1/2005 |
| KR | 20050004625 | 1/2005 |
| KR | 20050004626 | 1/2005 |
| KR | 20050065718 | 6/2005 |
| KR | 20050068357 | 7/2005 |
| KR | 20050089257 | 9/2005 |
| KR | 20070028012 | 3/2007 |
| KR | 100736819 | 7/2007 |
| KR | 100818561 | 4/2008 |
| KR | 20080075694 | 8/2008 |

(56) References Cited

FOREIGN PATENT DOCUMENTS

| | | |
|---|---|---|
| KR | 20090001293 | 1/2009 |
| KR | 20090090501 | 8/2009 |
| KR | 20110062719 | 6/2011 |
| KR | 20110075870 | 7/2011 |
| KR | 20120000652 | 1/2012 |
| KR | 101430906 | 8/2014 |
| MD | 2940 | 12/2005 |
| RU | 2135417 | 8/1999 |
| RU | 2182128 | 5/2002 |
| RU | 2193528 | 11/2002 |
| RU | 2264990 | 11/2005 |
| RU | 2324026 | 5/2008 |
| RU | 2373156 | 11/2009 |
| RU | 2381182 | 2/2010 |
| TW | I252268 | 4/2006 |
| TW | 200902790 | 1/2009 |
| TW | 201013008 | 4/2010 |
| TW | 201127948 | 8/2011 |
| TW | 201138638 | 11/2011 |
| UA | 22673 | 4/2007 |
| WO | 1999039749 | 8/1999 |
| WO | 2002036499 | 5/2002 |
| WO | 2003051780 | 5/2003 |
| WO | 2004104153 | 12/2004 |
| WO | 2006014080 | 1/2006 |
| WO | 2006129982 | 12/2006 |
| WO | 2007057077 | 5/2007 |
| WO | 2008075992 | 6/2008 |
| WO | 2011015429 | 2/2011 |
| WO | 2011067748 | 6/2011 |
| WO | 2011073697 | 6/2011 |
| WO | 2011110550 | 9/2011 |
| WO | 2011126395 | 10/2011 |
| WO | 2011139835 | 11/2011 |
| WO | 2012025943 | 3/2012 |
| WO | 2012031853 | 3/2012 |
| WO | 2012059992 | 5/2012 |
| WO | 2012077122 | 6/2012 |
| WO | 2012095665 | 7/2012 |
| WO | 2012095828 | 7/2012 |
| WO | 2012107422 | 8/2012 |
| WO | 2012140520 | 10/2012 |
| WO | 2012142025 | 10/2012 |
| WO | 2012150506 | 11/2012 |
| WO | 2012155269 | 11/2012 |
| WO | 2014196881 | 12/2014 |
| WO | 2015001870 | 1/2015 |
| WO | 2015084568 | 6/2015 |
| WO | 2015084569 | 6/2015 |

OTHER PUBLICATIONS

Liu et al., "Controlled Release of Biologically Active Silver from Nanosilver Surfaces," ACS Nano, 2010, pp. 6903-6913, vol. 4, No. 11.

Mitrano et al., "Presence of Nanoparticles in Wash Water from Conventional Silver and Nano-silver Textiles," ACS Nano, 2014, pp. 7208-7219, vol. 8, No. 7.

Putro et al., "Silver Nano Perfume Ejector to Destroy Bacteria for Clothes," AASIC, 2013, pp. 72-75.

\* cited by examiner

ANTIMICROBIAL BATCH DILUTION SYSTEM

REFERENCE TO RELATED APPLICATIONS

This application is a continuation in part of application Ser. No. 13/968,084 filed on Aug. 15, 2013 entitled ANTI-MICROBIAL DEVICE which is a continuation in part of application Ser. No. 13/402,771 filed on Feb. 22, 2012 entitled ANTI-MICROBIAL DEVICE, both having a common assigned with the present application, the disclosures of which are incorporated herein by reference.

BACKGROUND OF THE INVENTION

Field

The present invention is in the technical field of antimicrobial treatment. More particularly, the present invention provides a system employing metallic ion generation and dilution in desired concentrations, for batch storage and entrainment in a flow for use in antimicrobial treatment.

Related Art

Shortcomings of existing antimicrobial treatments can lead to the spread of infection through direct contact, airborne disease and waterborne disease. These diseases can be acquired by their victims from contacting contaminated surfaces, breathing air containing pathogens, or drinking pathogen containing water. Contaminated drinking water especially affects populations of second world and third world countries. The lack of inexpensive means to rid drinking water of harmful living microbes results in widespread illness and death in second world and third world countries. Similarly, contamination of fabrics or linens in uniforms, surgical scrubs, sheets, blankets, napkins, table cloths and similar materials by microbial pathogens can contribute to spread of disease.

Previous antimicrobial treatments require concentrated chemicals which are potentially or actually harmful to people and the environment. Such antimicrobial treatments also do not provide a lasting antimicrobial effect after the treatment has been administered. Existing antimicrobial treatments can also lead to immunization of evolved pathogens to the respective treatment. Such immunization of evolved pathogens can result in infections which cannot be treated with the conventional treatments that caused the pathogens to become immune.

Enterprises which specifically have problems with the spread of infectious diseases include, but are not limited to: the cruise line industry, hotel and gaming, professional sports teams, health and fitness clubs, nursing homes, and hospitals. Healthcare facilities currently have a growing problem with immunized pathogens being virtually untreatable with conventional methods. With such hospital infections, the harmful microbes are often carried in the linens and clothing provided by the hospital. Once hospital linens have been laundered and treated, they are susceptible to recontamination by microbes and pathogens. Pathogens carried by these linens can infect hospital patients and even cause death.

It is therefore desirable to provide an antimicrobial treatment system which may be employed directly in water supply systems to provide efficacious antimicrobial action.

SUMMARY OF THE INVENTION

The present invention is a device which releases a lasting, metallic, antimicrobial agent to which no known pathogens can become immune. Embodiments of the antimicrobial device disclosed provide an antimicrobial supply system having a process water supply and incorporating a metallic ion supply connected to the process water supply to provide a high ion concentrate to an output. A dilution reservoir is connected to the metallic ion supply output and has an input from the process water supply. A pump is connected to an output of the reservoir. A manifold connected to the pump provides a dilute concentrate to at least one washing system and a recirculation loop to the dilution reservoir for enhanced mixing of the dilute concentrate. An electronics control module is connected to a first flow controller between the process water supply and the metallic ion supply and a second flow controller between the metallic ion supply and the reservoir for dilution control establishing a desired metallic ion concentration.

BRIEF DESCRIPTION OF THE DRAWINGS

These and other features and advantages of the present invention will be better understood by reference to the following detailed description of exemplary embodiments when considered in connection with the accompanying drawings wherein.

DETAILED DESCRIPTION OF THE INVENTION

Figure 1:
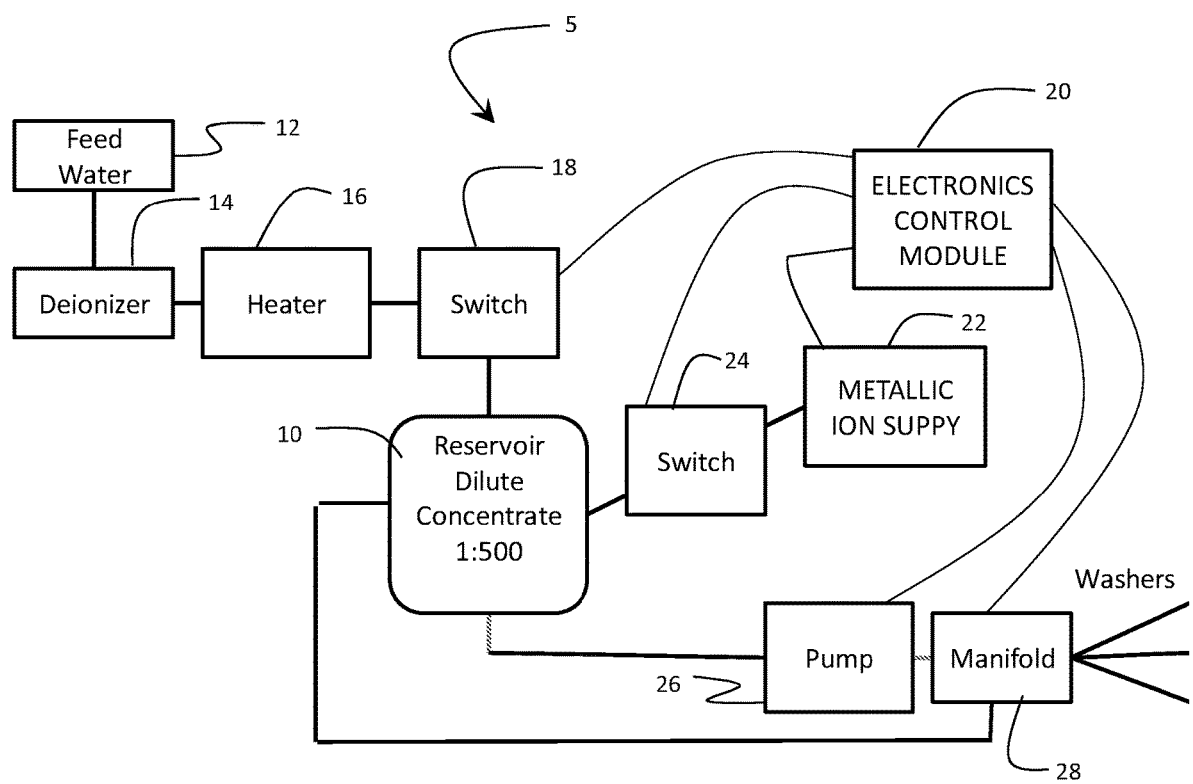
FIG. 1 is a block diagram of a batch dilution system for metallic ion antimicrobial agent generation, storage and distribution.

The embodiments disclosed herein provide a system for generation and batch dilution of metallic ions for use as an antimicrobial agent in processes such as commercial washing systems. As shown in FIG. 1, the system 5 incorporates a bulk reservoir 10. A feed water source 12, such as a house soft water system in a commercial washing facility, supplies water to a deionizing system 14 and heater 16 producing process water. A flow controller 18 operated under the control of an electronics control module 20 then provides the process water to the bulk reservoir 10. A metallic ion supply 22 adds antimicrobial ions into the process water forming a high ion concentrate for release through a second flow controller 24 to the bulk reservoir 10 for mixing with the process water to yield a desired dilute concentrate with metallic ions for use as an antimicrobial agent. The dilute concentrate is then provided from the reservoir 10 through a pump 26 to a manifold 28 for distribution to the commercial washers or similar systems. Recirculation of dilute concentrate from the manifold 28 to the reservoir 10 allows the reservoir to act as a buffer so that overall demand is equivalent to total mean demand on system, irrespective of spikes in demand (which are only then gated by outlet pumping rate).

Figure 2:
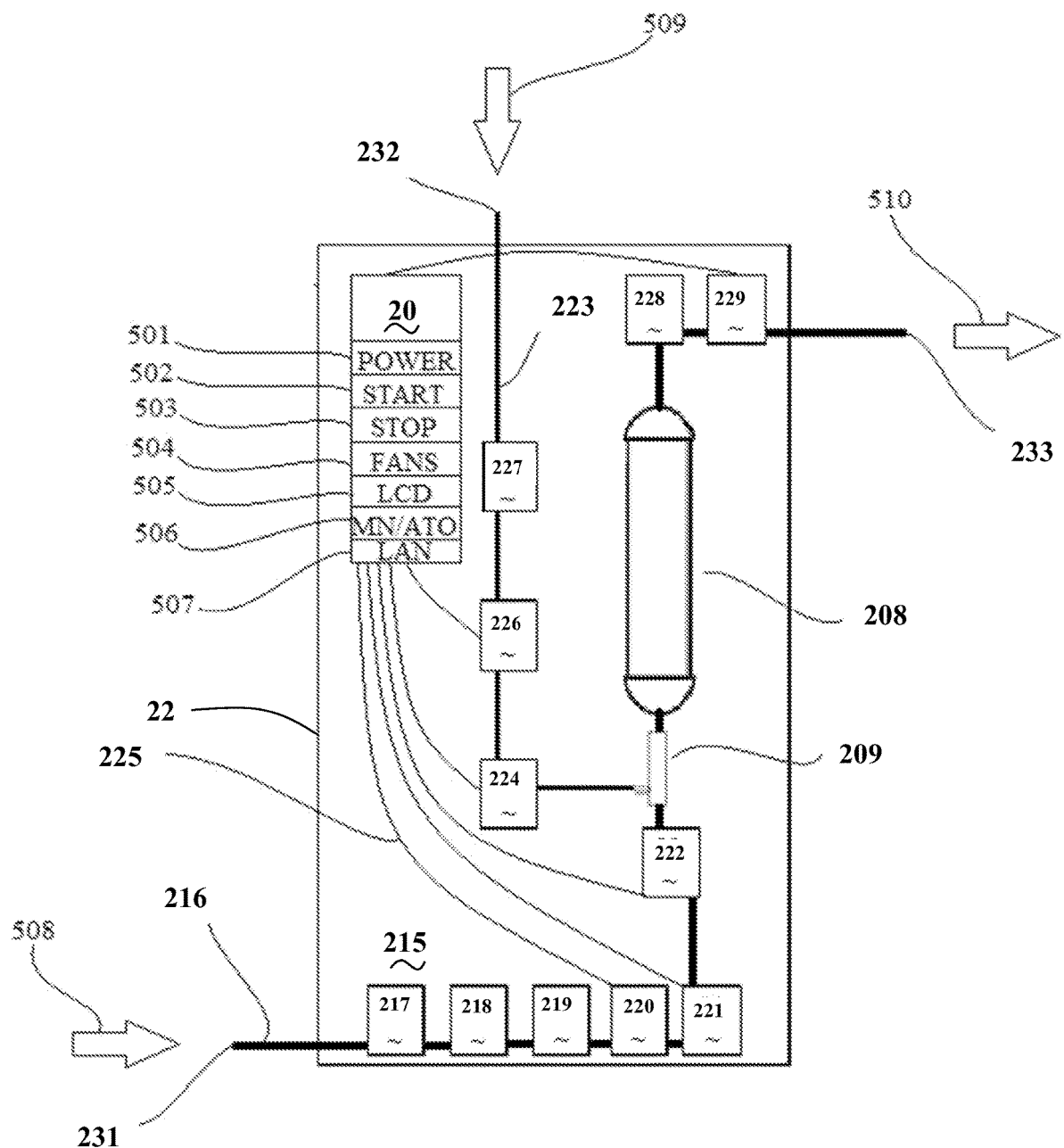
FIG. 2 is a system flow diagram of an exemplary embodiment of an electronic control and monitoring system, separate fluid lines, fluid diffusion sub-assembly and antimicrobial canister for metallic ion introduction.

FIG. 2 shows a system flow diagram of a first embodiment of the metallic ion supply 22 with a metallic ion supply canister 208 and fluid diffusion device 209, a manual water shut off 217, a water filter 219, water inlet 231, air inlet 232, an antimicrobial fluid combination outlet 233, the electronics module 20, which is a programmable device such as a microprocessor having software or firmware for specific INITIALIZATION; IDLE; PROCESS; and SHUTDOWN sequences, a solenoid water shut off valve 220, a water temperature sensor 221, a water pressure sensor 222, a air pressure sensor 224, a solenoid air shut off valve 226, and a flow sensor 229. The metallic ion supply canister 208 may be configured as disclosed in application Ser. No. 13/968,084.

The electronics module 20 has a power switch 501, manual start button 502, manual stop button 503, cooling fans 504, LCD display 505, and Manual Mode/Automatic Mode switch 506. The electronics module 20 also has wired and/or wireless connection 507 to local area internet networks to send data to any remote monitoring system with an internet connection. This internet capability also allows the system to be controlled wirelessly over the internet. For example, the system can be turned on and off over the internet and the allowable parameters for sensor detection can be adjusted over the internet. Because, the electronics module 20 can be controlled using the various buttons and switches on the electronics module 20 itself, or remotely though a local area network, the operator can control and monitor the present invention on site or offsite. The compilation of the electronics module programs provides the electronic control and monitoring system software. If the electronics module 20 receives electronic communication from one of the sensors, the electronic control and monitoring system software can be programmed to send signals or alerts to the operator via the wireless connection 507 or as messages to the LCD 504. The electronic control and monitoring system software also continuously logs data on system events and on received transmissions from the multiple sensors.

The solenoid water shut off valve 220, is used to start and stop water flow entering through inlet 231 as shown by arrow 508 through the system. The water temperature sensor 221 communicates electronically with the electronics module 20 in order to enable the electronic control and monitoring system software to log data or send an alert to the operator if water temperature deviates from a desired range. The water pressure sensor 222 communicates electronically with the electronics module 20 in order to enable the electronic control and monitoring system software to log data or send an alert to the operator if water pressure deviates from a desired range. The air pressure sensor 224 communicates electronically with the electronics module 20 in order to enable the electronic control and monitoring system software to log data or send an alert to the operator if air pressure deviates from a desired range. The solenoid air shut off 223 is used by the electronics module to start and stop air flow through the system entering at inlet 232 as indicated by arrow 509. The flow sensor 229 determines outlet flow from the system through outlet 233 as shown by arrow 510 and communicates electronically with the electronics module in order to enable the electronic control and monitoring system software to log data or send an alert to the operator if flow rate deviates from a desired range. A water pressure regulator 218, an air pressure regulator 227, and a flow reducer 228 provide additional for the metallic ion supply system.

The antimicrobial canister 208, the diffusion device 209, the manual water shut off 217, and water filter 219 are interconnected by the water line 216 and air line 223. The electronic devices are connected to the electronics module 20 by the electronic wiring 225. The electronic devices, mechanical devices, and the interconnecting plumbing lines and wires shown are all mounted to a mounting surface 215. An example set of parameters for the electronic control and monitoring system software might be programmed to monitor and control are the following: 140° F. water temperature, 15 psi of water pressure, 25 psi of air pressure, 2 gallon per minute (GPM) of flow rate, all with an acceptance range of within +/−15% before alerting the operator via warning and/or error messages displayed on the LCD screen on the electronics module 20 or through alerts transmitted over the local area network connection when the electronic control and monitoring system transmits a status report.

Figure 3:
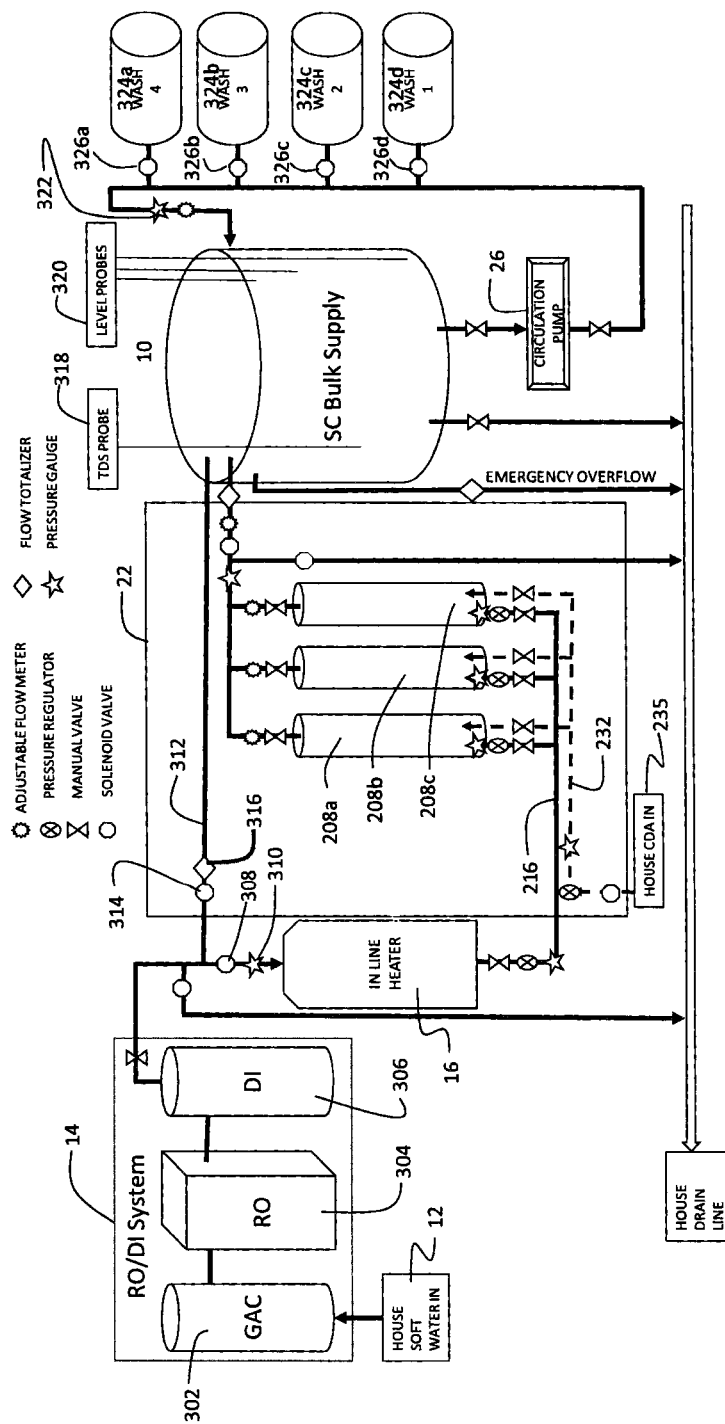
FIG. 3 is a block diagram of a detailed embodiment of a batch dilution system employing antimicrobial canisters for metallic ion introduction.

Details of an implementation of the first embodiment of the metallic ion supply for the batch dilution system are shown in FIG. 3. The deionizer 14 employs a granulated activated carbon (GAC) 302 receiving water from the house soft water source 12. Water drawn from the GAC flows through a reverse osmosis (RO) filter 304 and into a deionizing (DI) bath 306 from which process water is provided to the heater 16 through a solenoid valve 308 controlled by the electronic control module 20 acting as one element of the controller 18. A pressure gage 310 is provided for process control. Process water from the heater 16 is then provided to the metallic ion supply 22 as previously described with respect to FIG. 2. For the embodiment of FIG. 3, three canisters 208a, 208b and 208c each with the associated control valves described in FIG. 2 are employed. The canisters may be operated individually or in parallel for delivery of desired concentrations of metallic ions to the reservoir 10. Multiple canisters allow the system to keep up with demand. To achieve desired concentration of antimicrobial metallic ions in a water stream flowing through canisters 208 analysis demonstrates that the fluid combination entrains antimicrobial metallic ions as a log function with respect to uptake time (contact time of the fluid combination with the substrate in the canister), uptake function $Y=A \ln(x)-B$, where Y is the entrained ion concentration in parts per million (ppm) and x is the uptake time (seconds). Use of multiple canisters allows either an increase concentration (followed by dilution in reservoir at higher rate) or a higher total flowrate through the canisters with less bypass dilution as described subsequently, Deionization removes organic and ionic constituents from feed water. These constituents are considered contaminants. With contaminants removed, the equilibrium driving force for silver ion dissolution into the fluid combination increases as a result of the high purity (18 megaohm) of the DI fluid combination. Effectively, the DI fluid combination is a more effective solvent when ionizing/dissolving $Ag^0$ (metallic silver) to $Ag^+$ (aqueous silver ions), (such is the case with the finely woven metallic silver coated nylon cloth) when compared to city/tap feed water sources. Additionally, controllability and consistency of the system increase with anionic and organic contaminants removed. With reactive anions, such as chloride, removed from feed water via DI, kinetic conditions are consistent regardless of installation site beginning water quality. Anionic oxidants, such as chloride, affect the $Ag^0$ to $Ag^+$ dissolution process with varying degrees of impact depending on respective concentrations, by affecting the ability of dissolved oxygen to react with the surface of the silver coated nylon cloth or other metal bearing structure in the canister. In the absence of contaminants, the antimicrobial canister releases $Ag^+$ dependent upon the fluid combination dissolved oxygen content, temperature, and velocity (according to Reynold's number) and reaction time allowed between the fluid combination and silver coated nylon cloth inside the canister A dilution bypass 312 activated by solenoid valve 314 acting as a second element of controller 18 connects the process water from the deionizer 14 directly to the dilution reservoir 10. A flow totalizer 316 in the dilution bypass 312 is provided for process control by the electronic control module.

The dilution reservoir is filled and resupplied by activation of the metallic ion supply flowing hot process water from the heater 16 into one or more of the canisters 208a, 208b and 208c to provide high ion concentrate to the reservoir 10. A concentration probe such as a total dissolved solids (TDS) probe 318 (or in alternative embodiments a conductivity probe) measures ion concentration in the reservoir 10 which is provided to the electronics control module 20 and the electronic control module controls bypass solenoid valve 314 to add process water to the reservoir using flow totalizer 316 to achieve a desired dilute concentrate for fluid in the reservoir. A level probe system 320 provides at least a "tank full" level measurement and a "tank empty" measurement to the electronic control module for activation of the fill sequence. One or more intermediate fluid levels in the reservoir may be measured to allow intermediate fill or other process control.

As previously described, circulation pump 26 draws dilute concentrate from the reservoir 10 in a continuous flow loop through the manifold 28 thereby maintaining the mixed condition of the antimicrobial dilute concentrate solution. An adjustable flow meter 322 provides for flow measurement. For the embodiment shown, multiple individual Conventional Washer-Extractors (CWE) 324a-324d draw antimicrobial dilute concentrate solution from the manifold through solenoid valves 326a-326d as required in their wash cycles.

Figure 4:
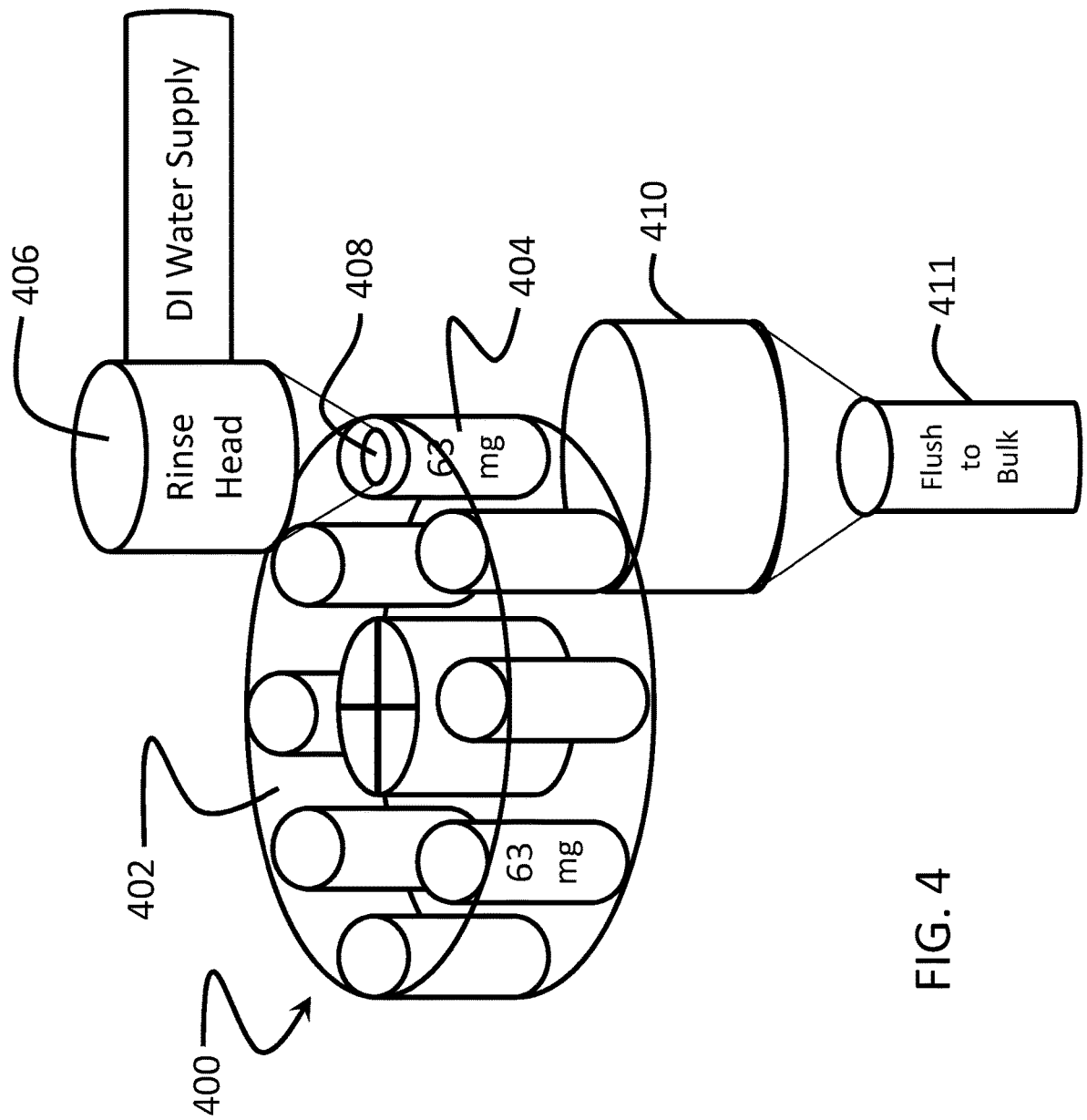
FIG. 4 is a representation of a second embodiment of a metallic ion supply.

A second embodiment of the metallic ion supply 22 is shown in FIG. 4. A pelletized metallic supply system 400 incorporates a revolving carousel 402 that supports multiple cartridges 404 containing a metallic or metallic compound powder (compressed/pelletized or loose), for an exemplary embodiment $AgNO_3$ powder. A rinse head 406 having a nozzle 408 sized to engage the cartridges 404 is connected to the deionizer 14 for process water supply. The carousel 402 aligns a cartridge 404 with the nozzle 408 and process water is sluiced through the cartridge into a capture container 410 providing a dose of high ion concentrate which is connected for flow into the reservoir 10 or alternative flow path through inlet 411.

Figure 5:
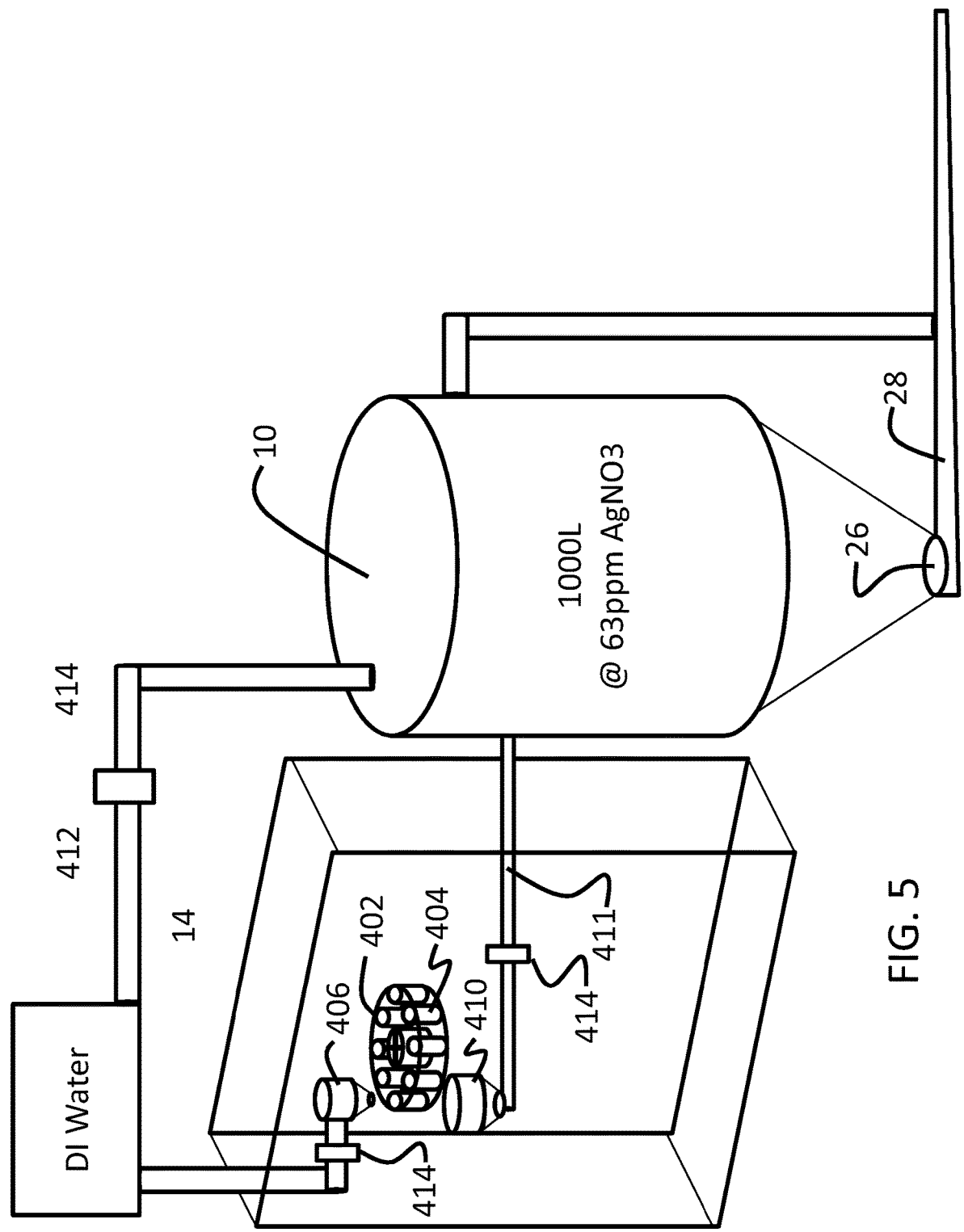
FIG. 5 is a block diagram of a detailed embodiment of a batch dilution system employing the metallic ion supply of FIG. 4; and, FIG. 6 is a schematic representation of an industrial washing system showing inlet flow from a batch dilution system for use with a Continuous Batch Washer (CBW).

As shown in FIG. 5, for a metallic ion supply system employing the pelletized metallic compound supply system 400 of FIG. 4, a dilution bypass 412 is provided to the reservoir 10 from the deionizer 14 supplying process water to the reservoir for dilution to the desired dilute concentrate. For an exemplary embodiment, reservoir 10 is a 1000 liter tank and cartridges 404 contain approximately 28.49 cc (or 14.47 cc compressed) of $AgNO_3$ powder. When diluted to the 1000 L volume of reservoir 10, a dilute concentrate of approximately 63 ppm is provided. Recirculation of the dilute concentrate by circulation pump 26 through manifold 28 maintains a mixed condition of the dilute concentrate. 1000 L storage tank will provide dilute concentrate through manifold 28 for one day to an inlet tunnel on the current largest washer in the world (Milnor CBW 250 lb) with a 3.4 L per tunnel injection to dose yielding 1 mg Ag/kg linen (63 ppm $AgNO3$ provides 40 ppm Ag as the active antimicrobial agent).

Aeration of the concentrate to enhance measurement accuracy with TDS or conductivity probes in the reservoir 10, as previously described, is provided by a diffusion device 414, which may be of comparable structure to the diffusion device 209 described with respect to FIG. 2, in one or more of the bypass line 412, inlet to the rinse head 406 or high ion concentrate inlet 411 to the reservoir 10. The desired aeration induced by the diffusion device is above 100% saturation (relative to published values).

Figure 6:
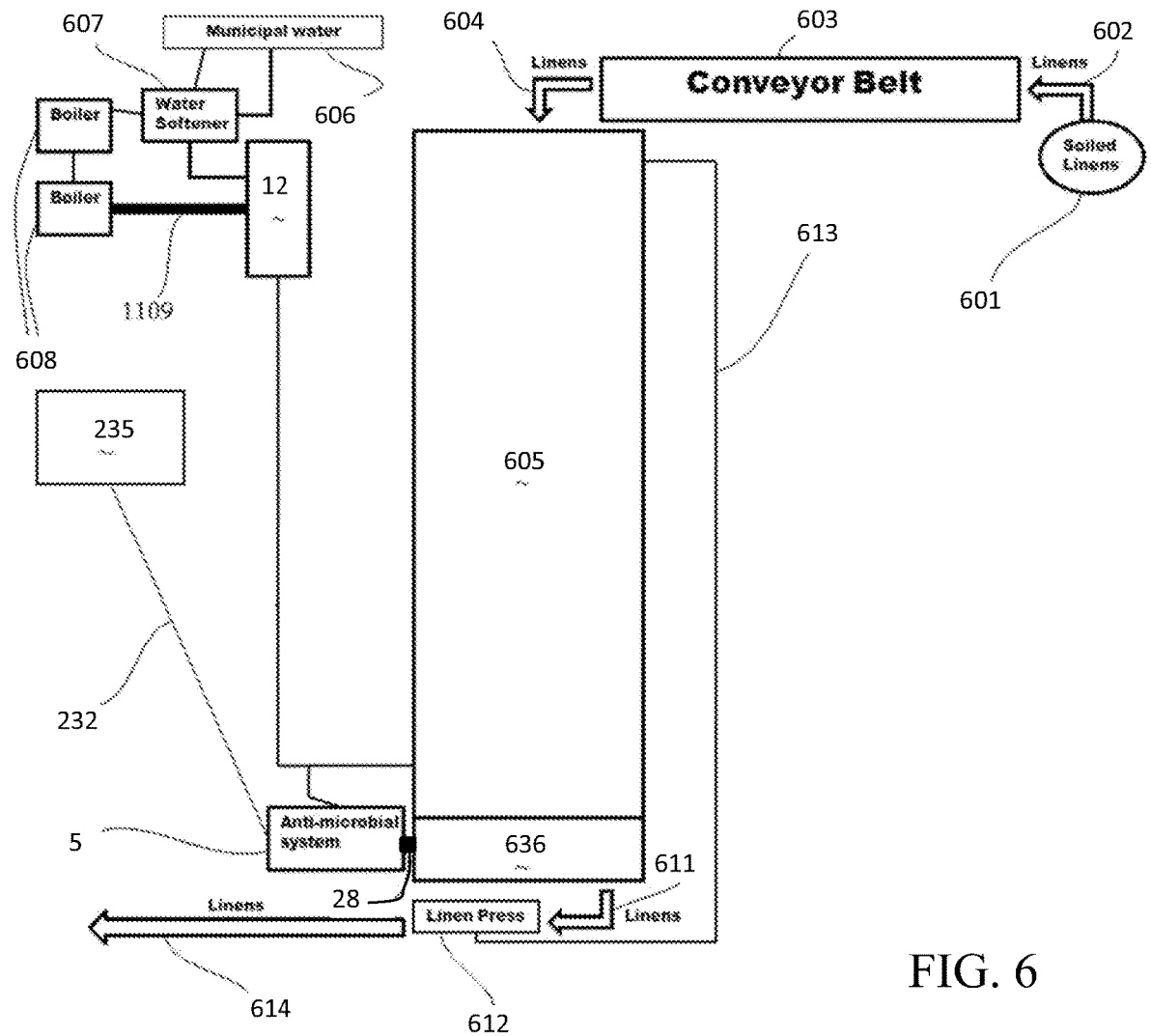

An example integration of the described embodiments into a commercial washing system is described in more detail with reference to FIG. 6 which shows a schematic of an industrial laundry facility. The washing machine may have multiple modules, thereby known as a Continuous Batch Washer (CBW). FIG. 6 depicts an instance where the present invention is integrated into a CBW process. Linens enter the system soiled 601 in batches of several hundred pounds and are transferred 602 manually by plant workers to a conveyor belt 603 that carries them to an elevated height where they are then gravity fed 604 into the CBW. The most effective integration of the present invention into this particular example of an industrial laundry facility is represented in FIG. 6 through placement of the antimicrobial and antimicrobial fluid combination outlet in manifold 28 which the example embodiment uses to inject the antimicrobial agent into the CBW rinse module 636. The example embodiments from FIG. 3 or 5 may be used in connection with water source 12, pressurized air source 235 and the CBW rinse module 636. The water source 12 receives municipal water 606 which is conditioned by a resin based, ion exchange, water softening system 607 and is heated using multiple boilers 608. The water source 12 provides water for the CBW wash modules 605 and delivers water to the system 5 for the embodiment shown. The antimicrobial fluid manifold 28 delivers the antimicrobial agent into the CBW rinse module 636. Once the linens have been treated with the antimicrobial agent in the CBW rinse module 636, they are automatically loaded 611 into a linen press 612, which presses excess rinse water out of the linens. That pressed water is recycled back into the beginning of the CBW system through rinse water recycle line 613. The rinse water recycle line 613 for the embodiment shown reintroduces the antimicrobial agent into the beginning of the wash cycle for added efficacy in antimicrobial treatment of the washed linens. Upon exiting the press 614, the linens may enter dryers or other machines within the laundry facility.

Having now described the invention in detail as required by the patent statutes, those skilled in the art will recognize modifications and substitutions to the specific embodiments disclosed herein. Such modifications are within the scope and intent of the present invention as defined in the following claims.

What is claimed is:

1. An antimicrobial supply system comprising:
 a metallic ion supply comprising a high metal ion concentrate supply and an output for providing the high metal ion concentrate;
 a dilution reservoir, wherein the dilution reservoir is a bulk reservoir, in fluid connection to the output of the metallic ion supply and having an input from a process water supply, and wherein the dilution reservoir is configured to form a dilute concentrate from (i) a process water received from a process water supply via the input of the dilution reservoir and (ii) the high metal ion concentrate received from the metallic ion supply via the output of the metallic ion supply;

a concentration probe in the dilution reservoir and configured to measure an ion concentration of the dilute concentrate in the dilution reservoir;

an output of the dilution reservoir coupled to at least one washing system; and, an electronics control module connected to (i) a first flow controller between a process water supply and the dilution reservoir and (ii) a second flow controller between the metallic ion supply and the dilution reservoir, wherein the electronics control module is configured to:
receive, from the concentration probe, an indication of the ion concentration of the dilute concentrate in the dilution reservoir, and
control, based on the indication of the ion concentration, the first flow controller and the second flow controller to achieve a desired ion concentration of the dilute concentrate in the dilution reservoir.

2. The antimicrobial supply system of claim 1, wherein the electronics control module is connected to a third flow controller that controls the flow of the dilute concentrate to the at least one wash system.

3. The antimicrobial supply system of claim 1, further comprising a deionizer for process water.

4. The antimicrobial supply system of claim 1, further comprising a reverse osmosis filter for process water.

5. The antimicrobial supply system of claim 1, further comprising a sensor in communication with the electronics control module,
wherein the sensor comprises at least one of a water temperature sensor, a water pressure sensor, an air pressure sensor, or a flow sensor.

6. The antimicrobial supply system of claim 5, wherein the sensor consists of the water temperature sensor.

7. The antimicrobial supply system of claim 5, wherein the sensor consists of the water pressure sensor.

8. The antimicrobial supply system of claim 5, wherein the sensor consists of the air pressure sensor.

9. The antimicrobial supply system of claim 5, wherein the sensor consists of the flow sensor, wherein senses a flow of the dilute concentrate supplied from the dilution reservoir to a manifold.

10. The antimicrobial supply system of claim 5, wherein the electronics control module is configured to:
receive data from the sensor; and
log the data received from the sensor.

11. The antimicrobial supply system of claim 5, wherein the electronics control module is configured to:
receive data from the sensor;
determine that the data received from the sensor deviates from a parameter associated with the sensor; and
responsive to a determination that the data received from the sensor deviates from the parameter, transmit, via a communication network, an alert signal to a remote system.

12. The antimicrobial supply system of claim 11, wherein the electronics control module is configured to:
receive, via the communication network, a control signal; and
responsive to the control signal, adjust the parameter associated with the sensor.

13. The antimicrobial supply system of claim 5, wherein the electronics control module is configured to:
receive data from the sensor;
transmit, via a communication network, the data to a remote monitoring system.

14. The antimicrobial supply system of claim 1, further comprising a manifold coupling the output of the dilution reservoir to the at least one washing system.

* * * * *